(12) United States Patent
Cox et al.

(10) Patent No.: US 6,440,162 B1
(45) Date of Patent: Aug. 27, 2002

(54) STENT HAVING INCREASED SCAFFOLDING EXPANDABLE BAR ARMS

(75) Inventors: Daniel L. Cox, Palo Alto; Andreina P. Gomez, Santa Clara; Timothy A. Limon, Cupertino, all of CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/626,407

(22) Filed: Jul. 26, 2000

(51) Int. Cl.[7] .................................................. A61F 2/06
(52) U.S. Cl. ...................................................... 623/1.15
(58) Field of Search ............................... 623/1.11, 1.12, 623/1.13, 1.14, 1.15, 1.16, 1.17, 1.18, 1.19, 1.2, 1.21, 1.22, 1.23; 606/108, 191, 192, 194, 198

(56) References Cited

U.S. PATENT DOCUMENTS

| 5,632,771 A | 5/1997 | Boatman et al. |
|---|---|---|
| 5,879,381 A * | 3/1999 | Moriuchi et al. ............... 623/1 |
| 5,922,020 A | 7/1999 | Klein et al. |
| 5,931,867 A | 8/1999 | Haindl |
| 6,013,091 A | 1/2000 | Ley et al. |
| 6,027,527 A | 2/2000 | Asano et al. |

FOREIGN PATENT DOCUMENTS

WO     WO 95/03010     2/1995

* cited by examiner

*Primary Examiner*—Henry J. Recla
*Assistant Examiner*—Vy Q. Bui
(74) *Attorney, Agent, or Firm*—Fulwider Patton Lee & Utecht, LLP (57) ABSTRACT

The invention is directed to a stent that is relatively flexible along its longitudinal axis but can be crimped or reduced to a very low profile while maintaining the ability to expand radially outwardly to any number of diameters to support a body lumen such as a coronary artery. The stent includes a plurality of cylindrical rings connected to each other by links. The cylindrical rings have curved portions that are attached by arms having slits that, when expanded, form apertures or holes to permit the stent to be reduced to a very low profile for delivery purposes, yet be able to expand the stent to various diameters and to provide sufficient vessel wall coverage when implanted.

10 Claims, 11 Drawing Sheets

STENT HAVING INCREASED SCAFFOLDING EXPANDABLE BAR ARMS

BACKGROUND OF THE INVENTION

This invention relates to expandable prostheses, generally referred to as stents, which are adapted to be implanted into a patient's body lumen, such as a blood vessel or coronary artery, to maintain the patency thereof. These devices are useful in the treatment of atherosclerotic plaque which develops in blood vessels, and is pretreated by angioplasty procedures, commonly referred to as percutaneous transluminal coronary angioplasty (PTCA) or an atherectomy which removes the plaque.

Stents are generally tubular-shaped devices which function to hold open a segment of a body lumen, blood vessel, or coronary artery. They are particularly suitable for use in supporting the vessel, holding back a dissected arterial lining which can occlude the fluid passageway, and are believed to be useful in reducing the likelihood of the development of restenosis.

Various means have been described to deliver and implant stents. One method frequently described for delivering a stent to a desired intraluminal location includes mounting and crimping the expandable stent on the expandable member of a catheter, such as a balloon, which is provided on the distal end of a catheter. The catheter is advanced to the desired location within the patient's body lumen and the balloon is subsequently inflated to expand the stent into a permanent expanded condition and then the balloon is deflated and the balloon and catheter removed from the body lumen leaving the stent permanently implanted.

Another method frequently described for delivering a stent to a desired intraluminal location includes mounting the stent on the distal end of a catheter, where the stent is a self-expanding stent formed from self-expanding stainless steel, or the so-called shape memory alloys such as nickel titanium (NiTi). The self-expanding stents are implanted by advancing the catheter to the desired location within the patient's body lumen, withdrawing a sheath so that the stent can self-expand into the body lumen, and then withdrawing the catheter and sheath leaving the stent permanently implanted. One of the difficulties encountered in using these prior art stents is the ability to tightly crimp the stent either on the balloon portion of the catheter or onto the distal end of the catheter. It is desired to have a low profile for delivery purposes yet be able to expand the stent to various diameters to hold open the vessel after implanting.

What has been needed and heretofor unavailable is a stent that can be crimped to a very small diameter thus reducing the profile of the stent as it is delivered through the vascular system, yet be able to expand to a wide range of diameters and yet maintain sufficient wall coverage of the vessel wall and maintain enough radial strength to hold open the body lumen into which it is expanded. The present invention satisfies this need.

SUMMARY OF THE INVENTION

The present invention is directed to a stent which is relatively flexible along its longitudinal axis to facilitate delivery through tortuous body lumens, but which is stiff and stable enough radially in an expanded condition to maintain the patency of the body lumen, such as a coronary artery, when implanted therein. The stent of the present invention is configured such that it can be crimped or reduced to a low profile, yet be expanded radially to any number of diameters yet maintain sufficient mechanical strength and radial support to hold open the body lumen into which it is expanded.

The stent of the invention generally includes a plurality of rings which are relatively independent in their ability to flex relative to one another. Interconnecting links (or struts) extend between adjacent rings to provide increased stability and are positioned so that the stent remains longitudinally flexible in all directions. At least some of the rings have curved sections attached to substantially straight arms where the arms have an expandable slit formed therein. The stent of the invention typically has a delivery configuration diameter, that is it is mounted on a catheter and tightly crimped thereon if it is of the expandable type, and is tightly pressed onto a catheter and covered with a sheath if it is of the self-expanding type. The expandable slits formed in the arms of the cylindrical rings permit the stent to be tightly crimped onto the catheter, and when expanded, the slits provide openings or apertures that allow the stent to expand radially outwardly and more evenly distribute bending stresses throughout the stent. Further, the openings in the arms provide better wall coverage than if the openings were not there.

In one embodiment of the invention, the stent is formed of a plurality of cylindrical rings, at least some of the rings having curved sections attached to substantially straight arms. The stent is formed of a deformable material so that it is mounted on the balloon portion of a catheter of either the rapid-exchange or over-the-wire type. At least some of the arms have an expandable slit formed therein, so that as the stent is expanded from a first delivery diameter to an expanded and implanted diameter, the slits open up to form holes or apertures. The cylindrical rings are interconnected by a plurality of links which are positioned so that the stent has uniform flexibility throughout its length. Alternatively, the arms are curved and have an expandable slit.

In another embodiment of the invention, the stent is formed of a plurality of rings, wherein at least some of the rings have curved sections attached to substantially straight arms, the arms having a slit formed therein. The rings are attached to each other by a plurality of links. In this embodiment, the stent is formed from a shape memory alloy, such as, for example, nickel titanium or nickel-titanium-vanadium. Typically, the stent is retained on the distal portion of a catheter of either the rapid-exchange or over-the-wire type, by a retractable sheath. The stent of the invention will expand from its delivery diameter to its expanded diameter when the sheath is removed or retracted proximally. Upon expansion, the slits in the arms of the cylindrical rings will expand to form openings or apertures. Alternatively, the arms are curved and have an expandable slit.

In another embodiment of the invention, the stent is formed of a plurality of rings, wherein at least some of the rings have curved sections attached to substantially straight arms, the arms having a slit formed therein. The rings are attached to each other by a plurality of links. In this embodiment, the stent is formed from a low memory metal, such as stainless steel, that is plastically deformed when expanded from a delivery diameter to an expanded diameter when implanted in a body lumen, such as a coronary artery. Typically, the stent is mounted on the balloon portion of a catheter, either of the rapid-exchange or over-the-wire type, and the balloon portion expands radially outwardly to expand the stent into contact with the body lumen. Upon expansion, the slits in the arms of the cylindrical rings will expand to form openings or apertures. Alternatively, the arms can be curved and have an expandable slit as well.

Other features and advantages of the present invention will become more apparent from the following detailed description of the invention, when taken in conjunction with the accompanying exemplary drawings.

DETAILED DESCRIPTION OF THE PREFERRED EMBODIMENTS

During PTCA procedures it is common to use a dilation catheter to expand a diseased area to open the patient's lumen so that blood freely flows. Despite the beneficial aspects of PTCA procedures and its widespread and accepted use, it has several drawbacks, including the possible development of restenosis and perhaps acute thrombosis and sub-acute closure. This recurrent stenosis has been estimated to occur in seventeen to fifty percent of patients despite the initial PTCA procedure being successful. Restenosis is a complex and not fully understood biological response to injury of a vessel which results in chronic hyperplasia of the neointima. This neonintimal hyperplasia is activated by growth factors which are released in response to injury. Acute thrombosis is also a result of vascular injury and requires systemic antithrombotic drugs and possibly thrombolytics as well. This therapy can increase bleeding complications at the catheter insertion site and may result in a longer hospital stay. Sub-acute closure is a result of thrombosis, elastic recoil, and/or vessel dissection.

Several procedures have developed to combat restenosis and sub-acute or abrupt closure, one of which is the delivery and implanting of an intravascular stent. Stents are widely used throughout the United States and in Europe and other countries. Generally speaking, the stents can take numerous forms, however, most common is a generally cylindrical hollow metal tube that holds open the vascular wall at the area that has been dilated by a dilation catheter.

The stents of the present invention can have virtually any configuration that is compatible with the body lumen in which they are implanted. The stent should be configured so that there is a substantial amount of open area and preferably the open area to metal ratio is at least 80%. The stent also should be configured so that dissections or flaps in the body lumen wall are covered and tacked up by the stent.

The stent of the present invention can be formed from a metal alloy taken from the group of metal alloys including superelastic alloys, shape memory alloys, and stainless steel alloys. Specifically, the present invention stent can be formed from shape memory or superelastic alloys so that the stent is self-expanding or it can be formed from a low memory stainless steel alloy so that the stent plastically deforms when expanded by the radial force from within, typically by a balloon from the balloon portion of a catheter.

Figure 1:
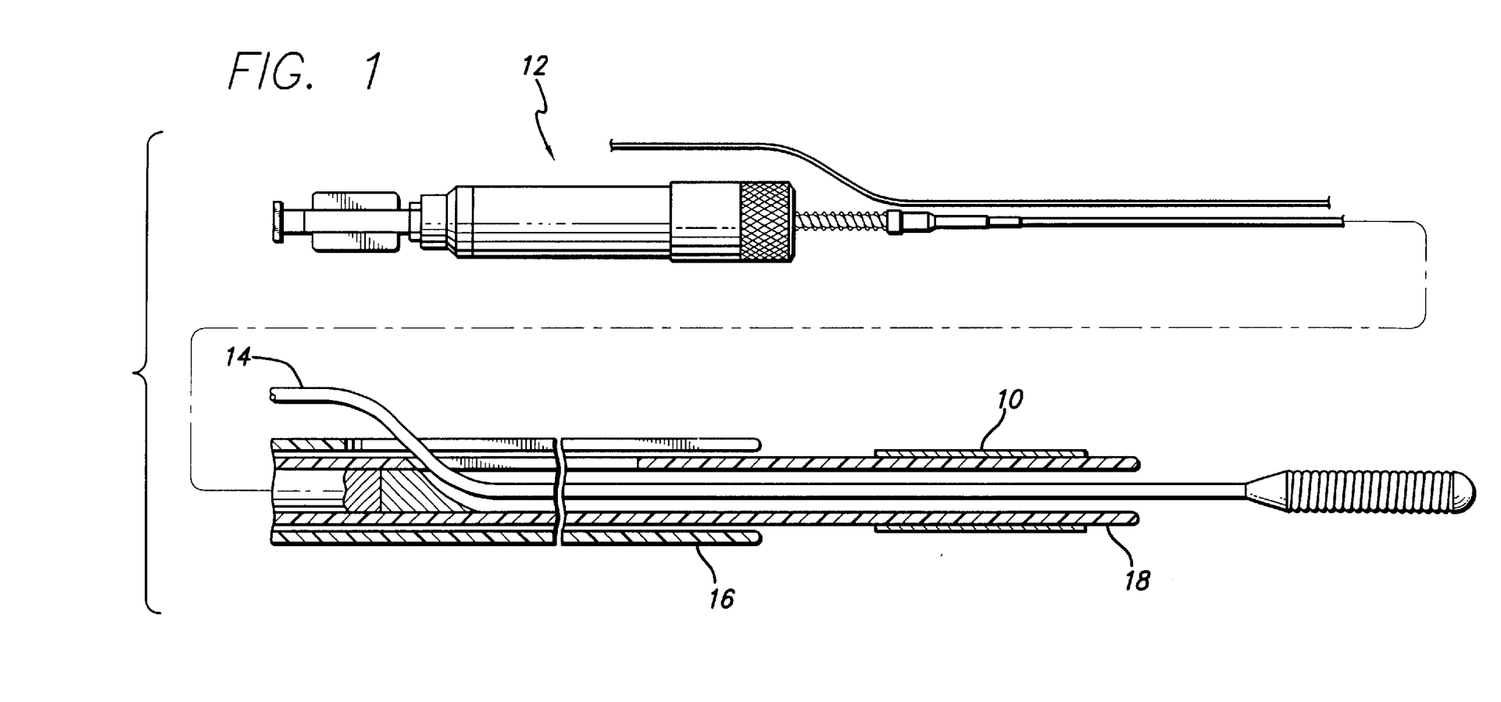
FIG. 1 is an elevational view, partially in section, of a stent delivery system embodying features of the invention.
Figure 2A:
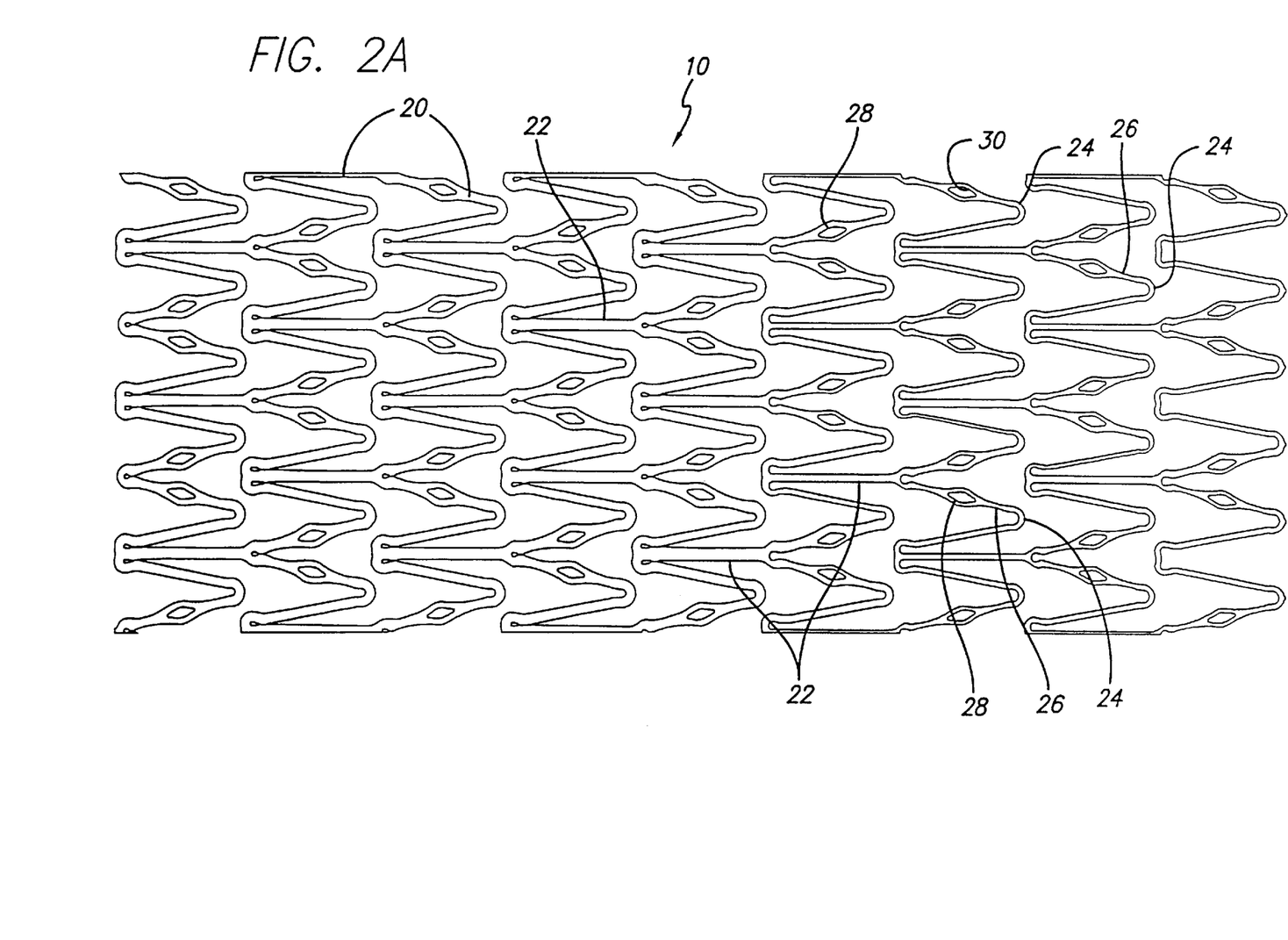
FIG. 2A is a plan view of a flattened section of the stent of the invention illustrating the inventive pattern.
Figure 2B:
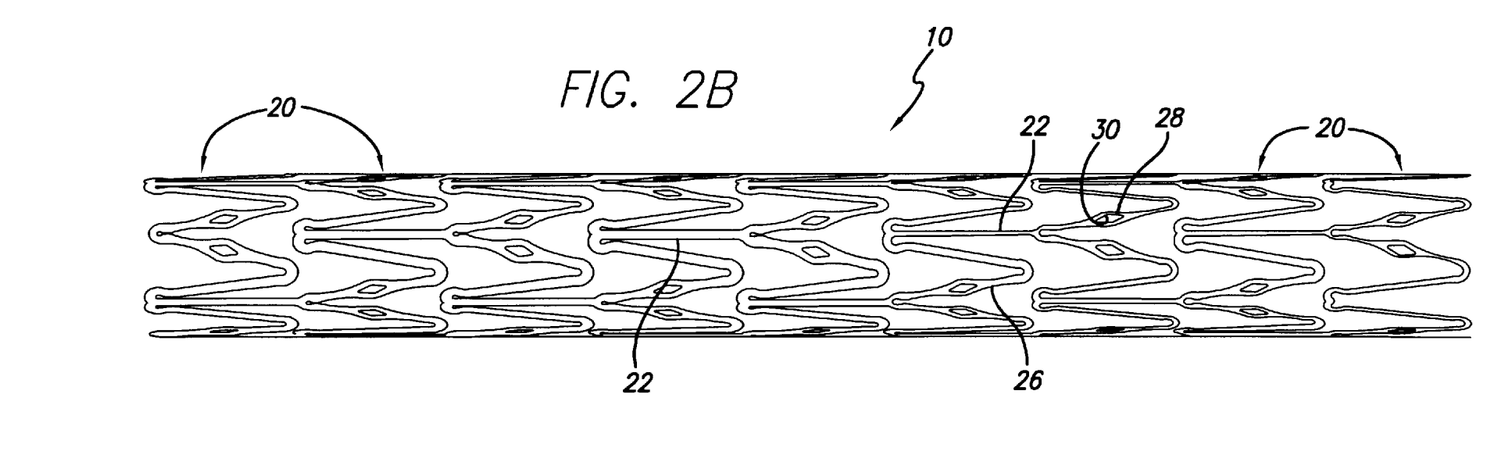
FIG. 2B is an elevational view of the stent of FIG. 2A depicting the stent formed into a cylindrical shape.
Figure 3:
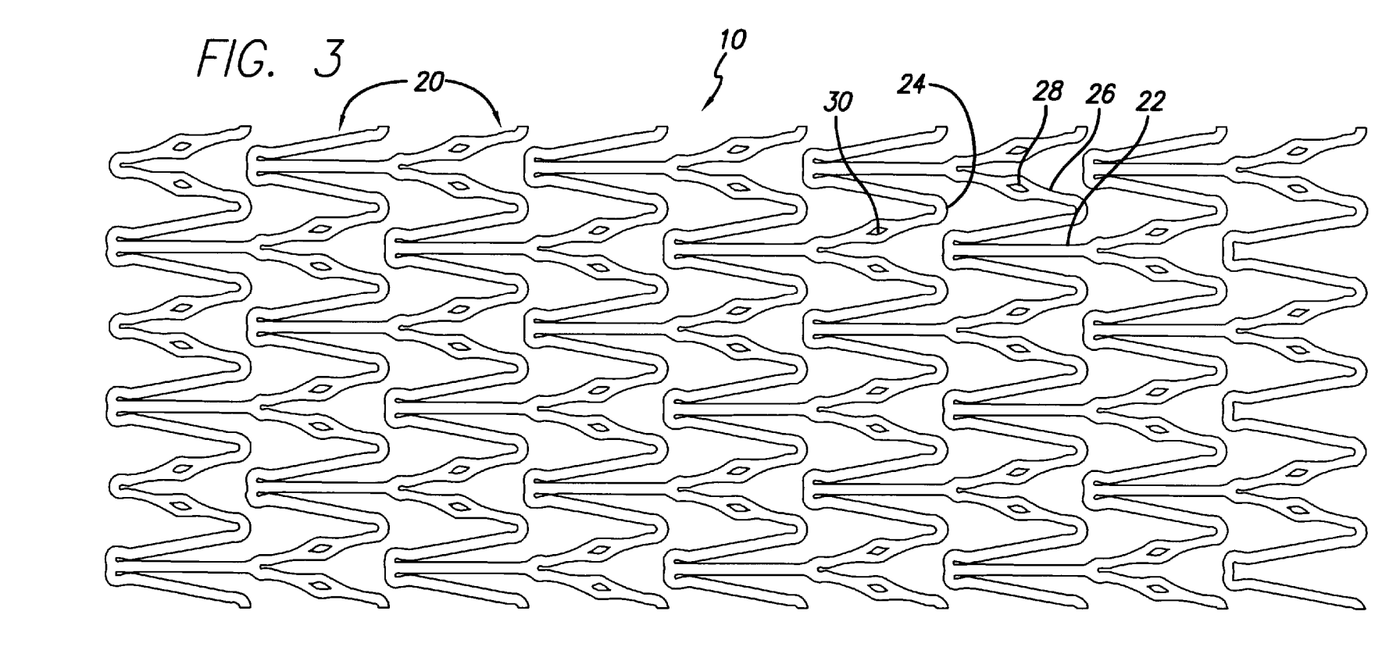
FIG. 3 is a plan view of a flattened section of the stent of the invention illustrating another embodiment of the stent pattern.
Figure 4:
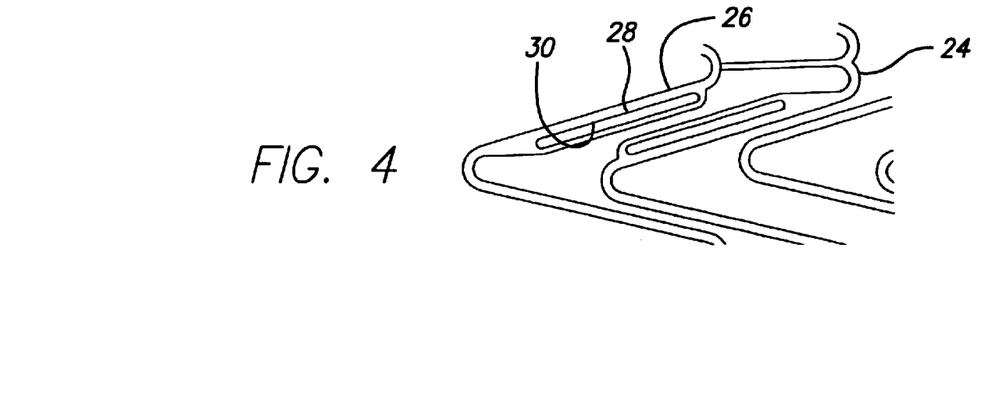
FIG. 4 is a section of a stent pattern depicting one embodiment of the invention.
Figure 5:
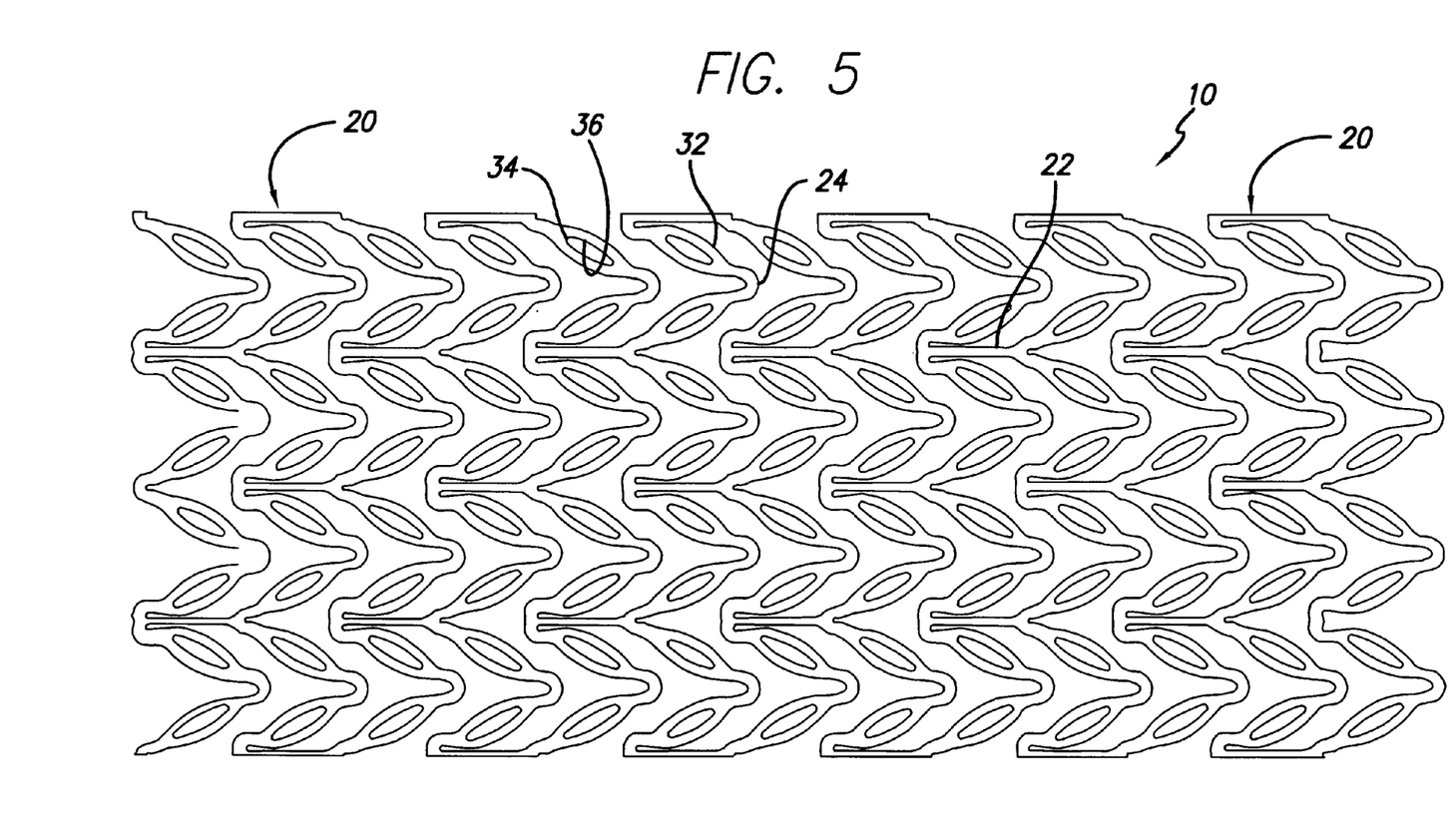
FIG. 5 is a plan view of a flattened section of the stent of the invention illustrating another embodiment of the invention.
Figure 6:
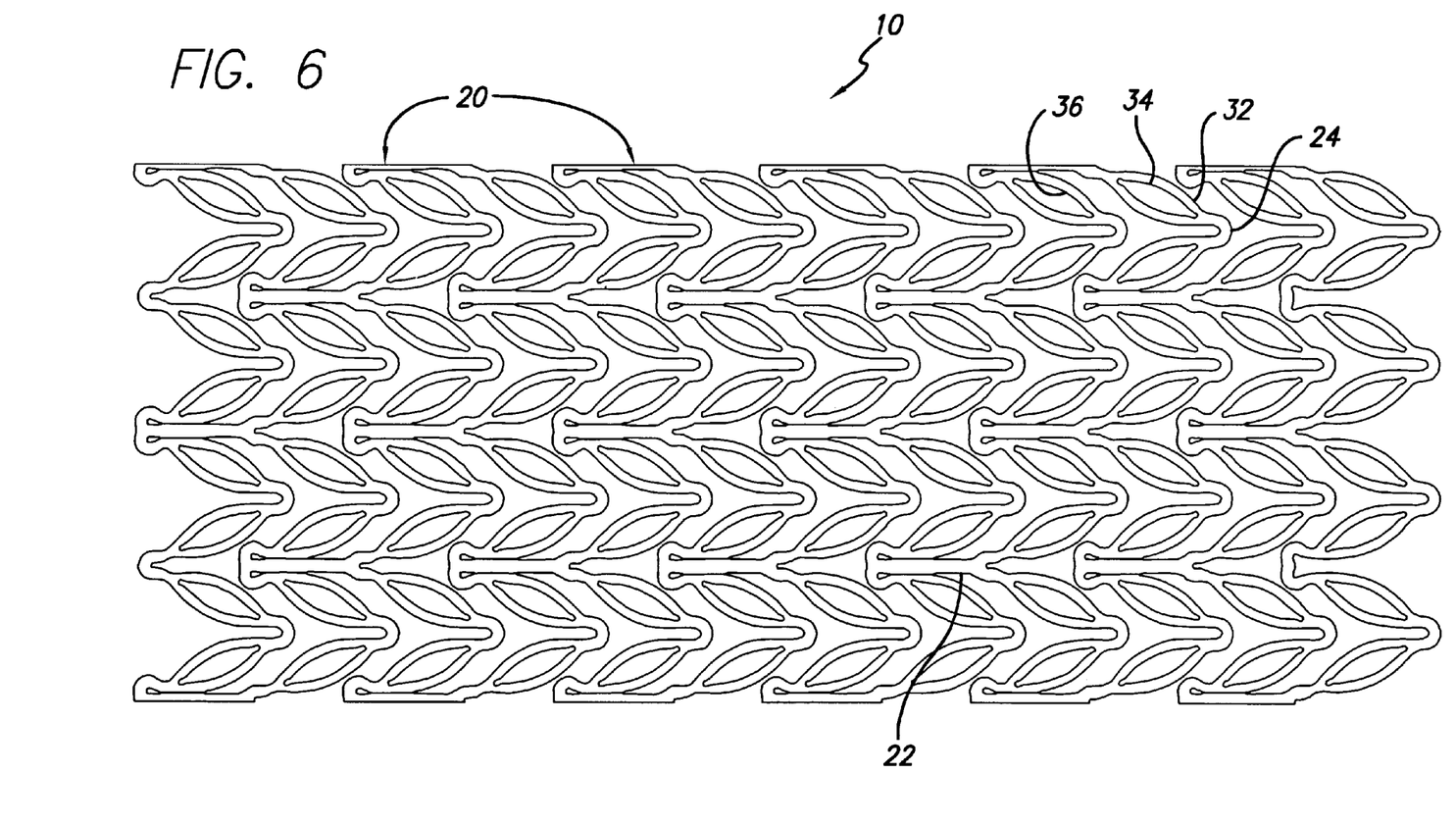
FIG. 6 is a plan view of a flattened section of the stent of the invention illustrating another embodiment of the invention.
Figure 7:
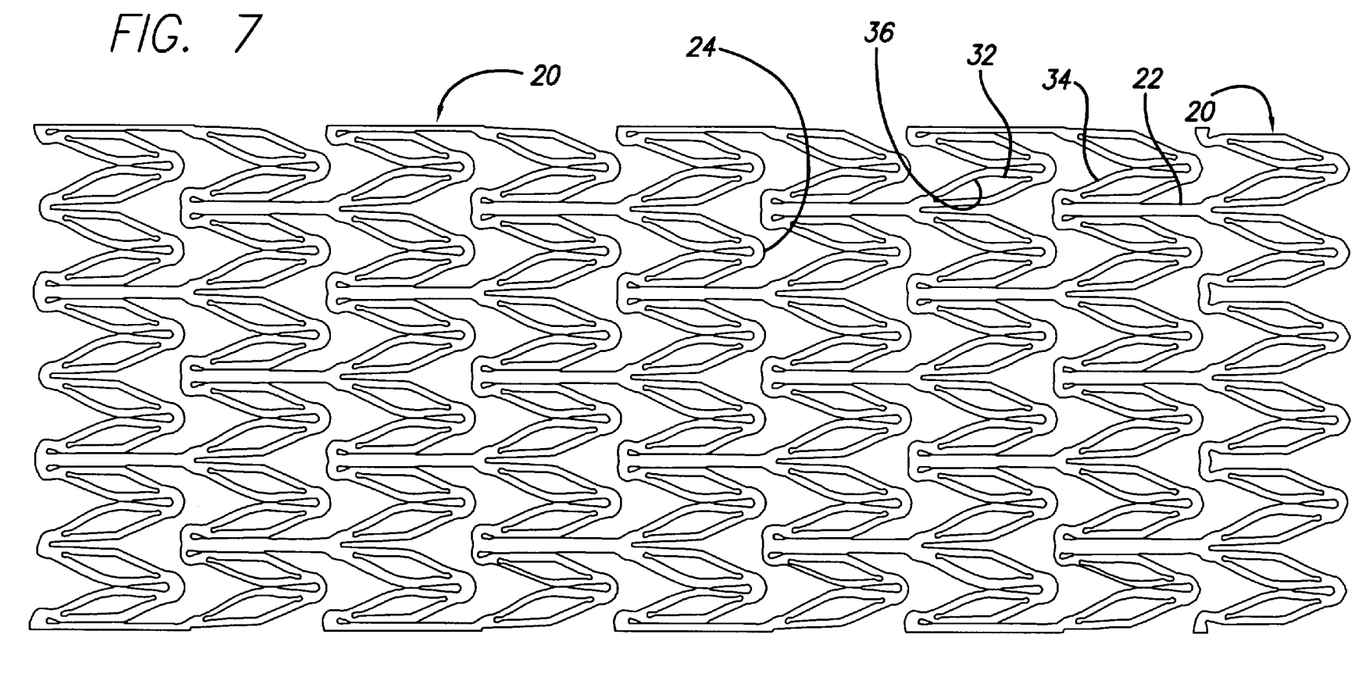
FIG. 7 is a plan view of a flattened section of the stent of the invention illustrating another embodiment of the invention.
Figure 8:
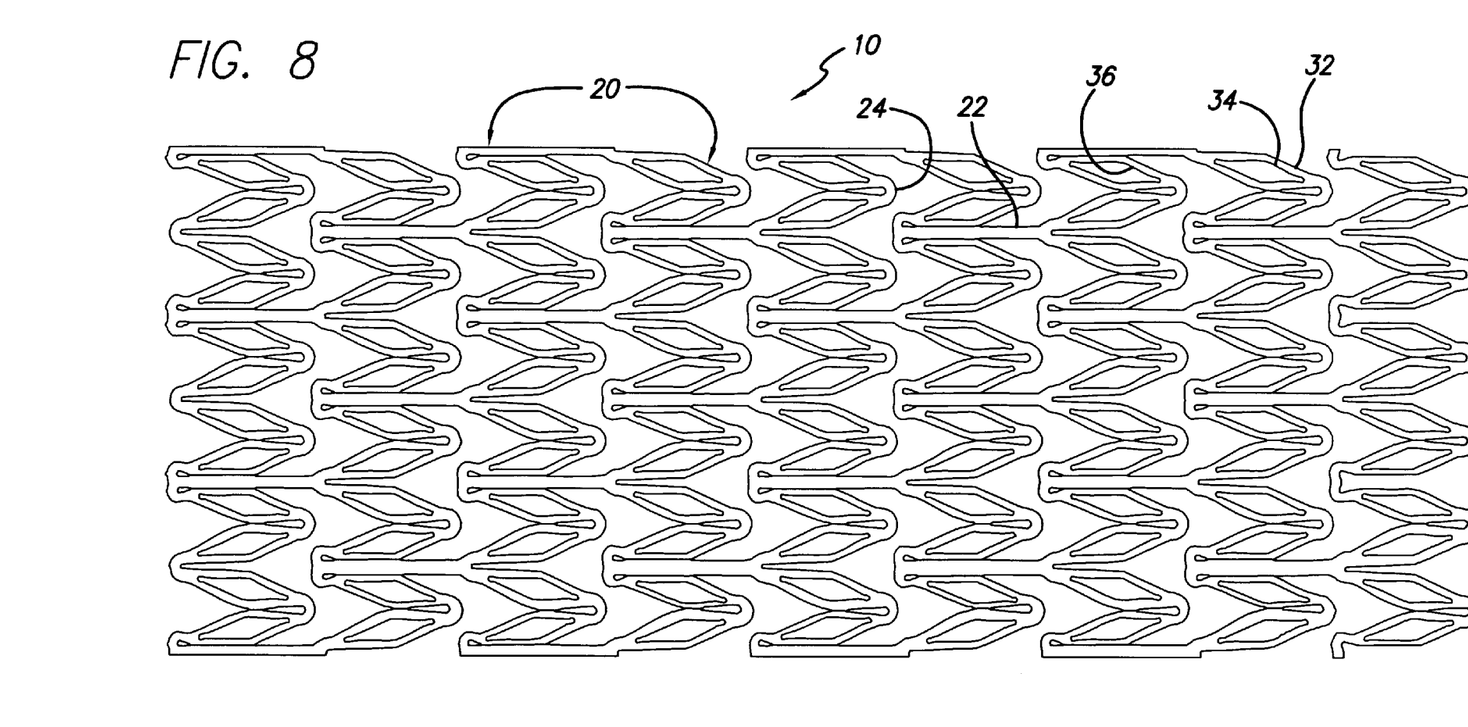
FIG. 8 is a plan view of a flattened section of the stent of the invention illustrating another embodiment of the invention.
Figure 9:
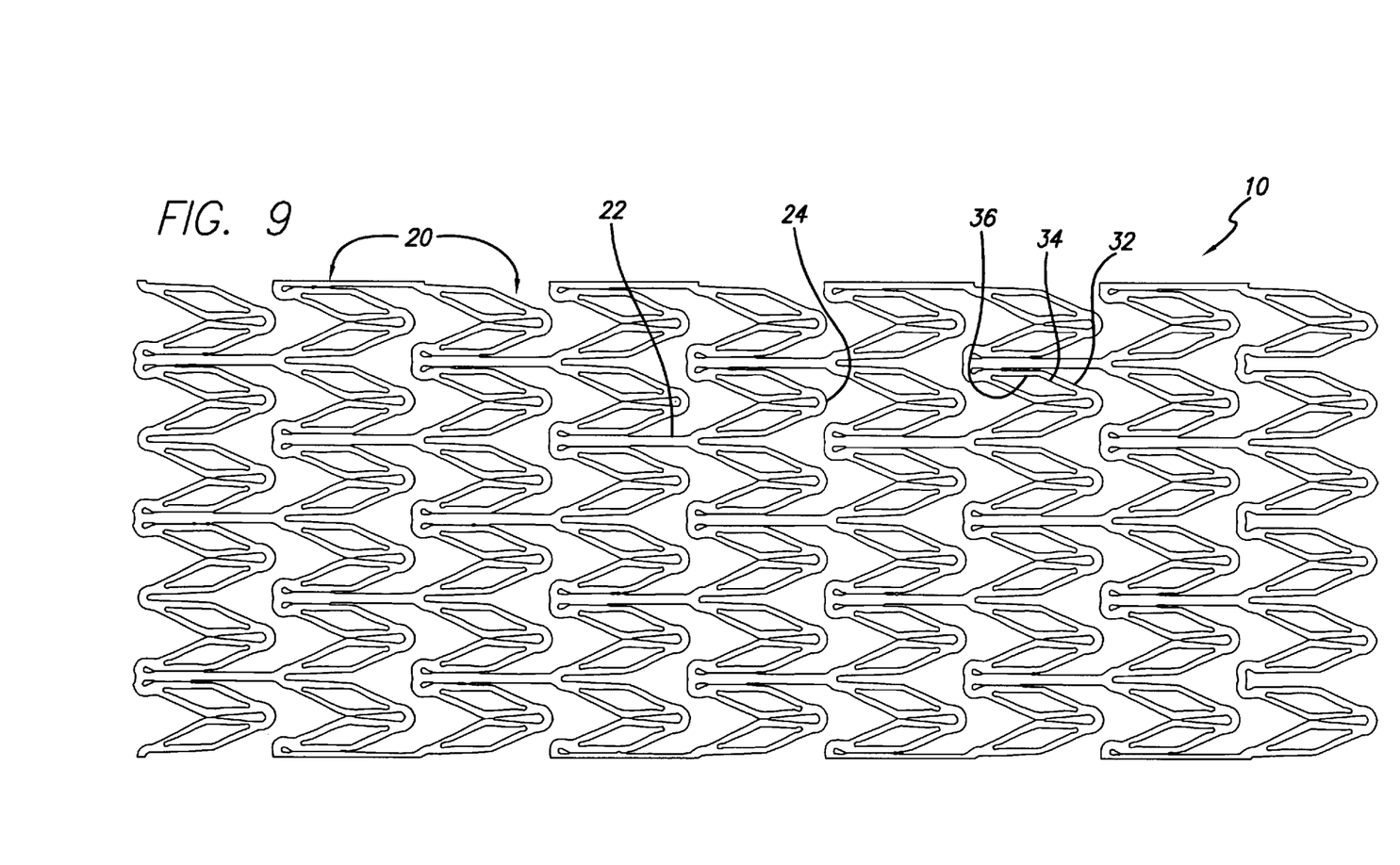
FIG. 9 is a plan view of a flattened section of the stent of the invention illustrating another embodiment of the invention.

Referring to FIG. 1, in one preferred embodiment, stent 10 of the present invention is formed partially or completely of alloys such as Nitinol (NiTi) which have superelastic (SE) characteristics or shape memory effects (SME) and are delivered on a rapid-exchange catheter in a known manner.

FIG. 1 illustrates a rapid exchange stent delivery system that includes a manipulating device 12, a guide wire 14, a delivery sheath 16, and a rapid-exchange catheter 18. This delivery system is just one example of a delivery system that may be used with the present invention. In keeping with the invention, stent 10 is mounted over the catheter and the delivery sheath is positioned over the self-expanding stent to hold it in position. It is noted that in this embodiment, the stent is of the self-expanding type requiring delivery sheath 16 to hold the stent in its compressed configuration until the stent is delivered in the body lumen. In this embodiment, the stent can be formed of Nitinol having superelastic characteristics or shape memory as described herein.

In keeping with the invention, the stent 10 is shown more clearly in FIGS. 2–9 in a flattened state. Generally speaking, the stent of the present invention would never be in the flattened state as shown in the drawings, however, it is shown in this manner for ease of illustration. Typically, the stent would be formed from a tubular member by laser cutting a pattern into a solid tubular member. The stent 10 includes a plurality of cylindrical rings 20 that extend 360° around the cylinder and generally are independently expandable from each other. That is, one cylindrical ring can be expanded while an adjacent cylindrical ring may expand at a different rate or to a different diameter. The cylindrical rings are attached to each other by a plurality of links 22 which can be of various thicknesses or lengths depending upon the application. The cylindrical rings preferably are formed from curved sections 24 having substantially straight arms 26 extending therefrom. A plurality of expandable slits 28 are formed in the substantially straight arms so that when the stent is expanded from its delivery diameter to its expanded diameter, the slits expand to form an aperture or hole 30. The expandable slit allows for the stent to be crimped more tightly onto the catheter when the stent is in the delivery diameter configuration. Thus, the stent of the present invention has advantages over prior art stents wherein the stent can be crimped more tightly and to a smaller diameter, yet still be expanded to any number of various diameters to support a body lumen, such as a coronary artery. Further, the expandable slits 28 provide some flexibility to the straight arms 26, that is, the straight arms are more flexible with the expandable slit than without it.

In one embodiment of the invention, as shown in FIGS. 5–9, the cylindrical rings 20 have curved sections 24 that are attached to curved arms 32. The curved arms have a plurality of expandable slits 34 formed therein, the expandable slits being essentially closed when the stent is in its delivery diameter configuration. When the stent is expanded to its implanted diameter, the slits open up to form a plurality of apertures or holes 36 which increase stent flexibility and provide good vessel wall coverage. Further, as described, the slits 34 can be crimped down more tightly when the stent is in its delivery diameter configuration, which is an advantage over prior art stents.

The stent of the invention as shown in FIGS. 2–9, can be formed from self-expanding alloys such as Nitinol (NiTi) or stainless steel that has high memory characteristics and does not plastically deform. It is contemplated that when the stent is formed from a Nitinol material, that it have either superelastic or shape memory properties.

Superelastic refers to an isothermal reaction; i.e., stress-induced martensite (SIM). Alloys having superelastic properties generally have at least two phases: a martensite phase, which has a relatively low tensile strength and which is stable at relatively low temperatures, and an austenite phase, which has a relatively high tensile strength and which is stable at temperatures higher than the martensite phase. Superelastic characteristics generally allow the metal stent to be deformed by collapsing and deforming the stent and creating stress which causes the NiTi to change to the martensite phase. The stent is restrained in the deformed condition to facilitate the insertion into a patient's body, with such deformation causing the phase transformation. Once within the body lumen, the restraint on the stent is removed, thereby reducing the stress therein so that the superelastic stent can return to its original undeformed shape by the transformation back to the austenite phase.

When stress is applied to a specimen of a metal such as Nitinol exhibiting superelastic characteristics at a temperature at or above which the transformation of the martensite phase to the austenite phase is complete, the specimen deforms elastically until it reaches a particular stress level where the alloy then undergoes a stress-induced phase transformation from the austenite phase to the martensite phase. As the phase transformation proceeds, the alloy undergoes significant increases in strain, but with little or no corresponding increases in stress. The strain increases while the stress remains essentially constant until the transformation of the austenite phase to the martensite phase is complete. Thereafter, further increase in stress is necessary to cause further deformation. The martensitic metal first yields elastically upon the application of additional stress and then plastically with permanent residual deformation.

If the load on the specimen is removed before any permanent deformation has occurred, the martensitic specimen will elastically recover and transform back to the austenite phase. The reduction in stress first causes a decrease in strain. As stress reduction reaches the level at which the martensite phase transforms back into the austenite phase, the stress level in the specimen will remain essentially constant (but substantially less than the constant stress level at which the austenite transforms to the martensite) until the transformation back to the austenite phase is complete; i.e., there is significant recovery in strain with only negligible corresponding stress reduction. After the transformation back to austenite is complete, further stress reduction results in elastic strain reduction. This ability to incur significant strain at relatively constant stress upon the application of a load and to recover from the deformation upon the removal of the load is commonly referred to as superelasticity or pseudoelasticity.

The superelastic alloy is preferably formed from an alloy consisting essentially of about 30% to about 52% titanium and the balance nickel and up to 10% of one or more additional alloying elements. Such other alloying elements may be selected from the group consisting of up to 3% each of iron, cobalt, platinum, palladium, and chromium, and up to about 10% copper and vanadium. As used herein, all references to percent composition are atomic percent unless otherwise noted.

In another preferred embodiment, a NiTi stent with SME (shape memory effect) is heat-treated at approximately 500° C. The stent is mechanically deformed into a first, smaller diameter for mounting on a catheter delivery system, such as the delivery system of FIG. 1. In order to implant this stent, 45° C. heat is applied causing the stent to expand to its fully expanded larger diameter and contact the arterial wall of the artery. The application of 45° C. of heat is compatible with most applications in the human body, but it is not to be limited to this temperature as higher or lower temperatures are contemplated without departing from the invention. The 45° C. temperature can be achieved in a conventional manner well known in the art such as by warm saline injected into the delivery catheter.

The shape memory characteristics allow the devices to be deformed to facilitate their insertion into a body lumen or cavity and then be heated within the body so that the device returns to its original shape. Again, alloys having shape memory characterisitcs generally have at least two phases: a martensite phase, which has a relatively low tensile strength and which is stable at relatively low temperatures, and an austenite phase, which has a relatively high tensile strength and which is stable at temperatures higher than the martensite phase.

Shape memory characteristics are imparted to the alloy by heating the metal at a temperature above which the transformation from the martensite phase to the austenite phase is complete; i.e., a temperature above which the austenite phase is stable. The shape of the metal during this heat treatment is the shape "remembered." The heat-treated metal is cooled to a temperature at which the martensite phase is stable, causing the austenite phase to transform to the martensite phase. The metal in the martensite phase is then plastically deformed, e.g., to facilitate the entry thereof into a patient's body. Subsequent heating of the deformed martensite phase to a temperature above the martensite to austenite transformation temperature causes the deformed martensite phase to transform to the austenite phase. During this phase transformation the metal reverts back to its original shape.

The recovery or transition temperature may be altered by making minor variations in the composition of the metal and in processing the material. In developing the correct composition, biological temperature compatibility must be determined in order to select the correct transition temperature. In other words, when the stent is heated, it must not be so hot that it is incompatible with the surrounding body tissue. Other shape memory materials may also be utilized, such as, but not limited to, irradiated memory polymers such as autocrosslinkable high density polyethylene (HDPEX).

Shape memory alloys are known in the art and are discussed in Shape Memory Alloys, *Scientific American*, Volume 281, pages 74–82 (November 1979), incorporated herein by reference.

Shape memory alloys undergo a transition between an austenitic state and a martinsitic state at certain temperatures. When they are deformed while in the martinsitic state they will retain this deformation as long as they are retained in this state, but will revert to their original configuration when they are heated to a transition temperature, at which time they transform to their austenitic state. The temperatures at which these transitions occur are affected by the nature of the alloy and the condition of the material. Nickel-titanium-based alloys (NiTi), wherein the transition temperature is slightly lower than body temperature, are preferred for the present invention. It is desirable to have the transition temperature set at just below body temperature to insure a rapid transition from the martinsitic state to the austenitic state when the stent is implanted in a body lumen.

Figure 10:
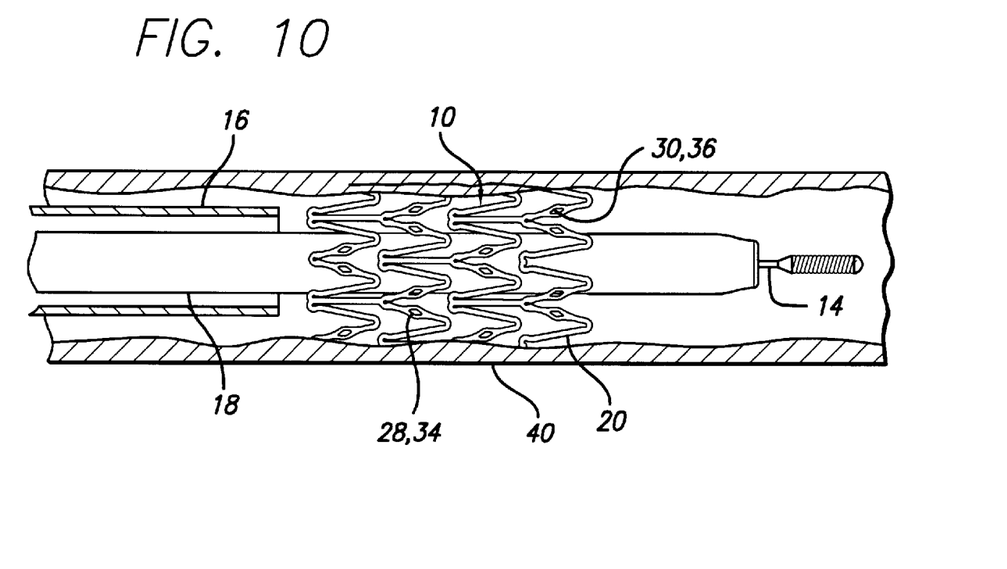
FIG. 10 is an elevational view, partially in section, depicting the stent of the invention being implanted to repair a vessel.
Figure 11:
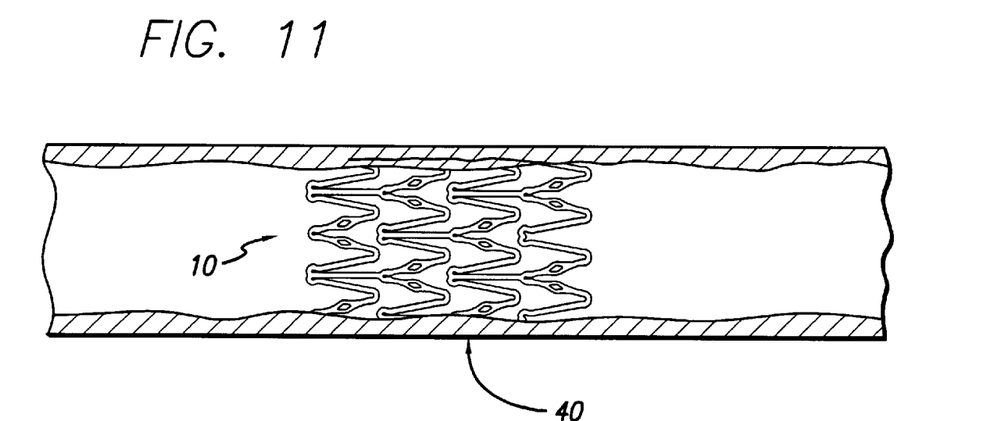
FIG. 11 is an elevational view, partially in section, depicting the expanded stent of the invention within the vessel after withdrawal of the delivery catheter.

The stent of the present invention, as depicted in FIGS. 2–9, are implanted in a body lumen, such as a coronary artery, in a known manner and as illustrated in FIGS. 10 and 11. Typically, when a self-expanding stent 10 is mounted on a catheter, such as of the rapid-exchange type catheter 18, sheath 16 overlies the stent to hold the stent onto the distal portion of the catheter. After the guide wire 14 is positioned within the body lumen 40, the catheter assembly with the sheath overlying and retaining the stent on the catheter, are advanced to the target site within the body lumen. The sheath is withdrawn proximally in a known manner to expose the stent which will self-expand into contact with the body lumen. As the stent expands, the cylindrical rings 20 expand radially outwardly, and the expandable slits 28,34, will expand to form apertures 30,36. After the stent expands into contact with the body lumen, the catheter and sheath are withdrawn from the body lumen as shown in FIG. 11. The guide wire may be left in place for further procedures, such as using a high pressure balloon to more firmly implant and embed the stent into the body lumen. Thereafter, the guide wire also is withdrawn from the patient's vascular system.

If the stent of the present invention is formed from a shape memory alloy, as described herein, it may be necessary to raise the temperature of the stent in order for it to expand radially outwardly into contact with the body lumen 40. There are known methods for heating the stent so that it changes from the martensitic to the austenitic state, such as injecting heated saline through the catheter into the area of the stent to raise its temperature, and thereby causing the phase transformation to the austenitic state where the stent will remain expanded against the vessel wall.

Figure 12:
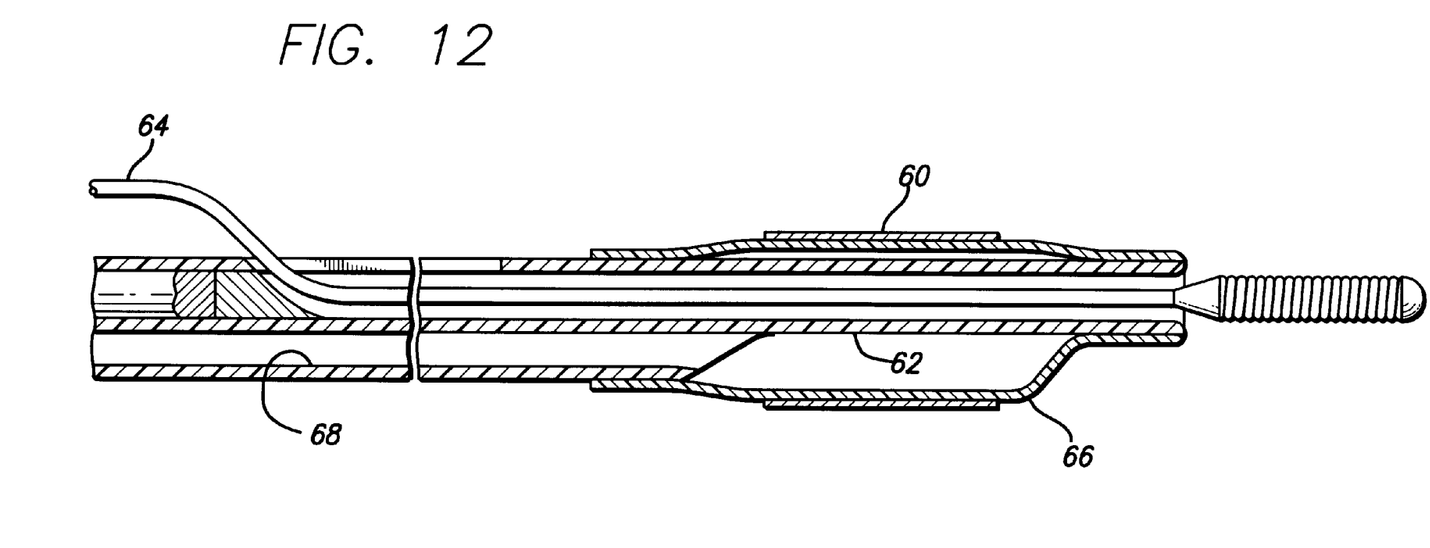
FIG. 12 is a partial cross-sectional view depicting another stent delivery system embodying features of the present invention.

In an alternative embodiment of the invention, as shown in FIG. 12, stent 60 is formed from stainless steel that has a low memory composition so that the metal plastically deforms when expanded. Stents having low memory metal are well known and are typically are expanded by the balloon portion of a catheter. In this embodiment, catheter 62 is of the rapid-exchange type and includes a guide wire 64 upon which the catheter is advanced within the body lumen. The stent is mounted on a balloon 66 that is in fluid communication with an inflation lumen 68. Stent 60, which can have any of the embodiments shown in FIGS. 2–9, is crimped tightly onto the balloon so that its delivery diameter has a low profile as the catheter and stent are advanced over the guide wire through a patient's vascular system and into a body lumen, such as a coronary artery. Once at the target site, the balloon portion of the catheter is inflated in a conventional manner thereby expanding the stent into contact with the artery wall. As previously described, the cylindrical rings expand radially outwardly into contact with the artery wall, and the expandable slits also expand to form the apertures as described. Unlike the self-expanding stent, the balloon expandable stent when expanded, may not form apertures as readily as does the self-expanding stent. However, apertures will form to some extent and provide sufficient wall coverage and yet permit the stent to be tightly crimped onto the balloon portion of the catheter.

The stent of the present invention can be made in any conventional manner such as by laser cutting, chemical etching, or electron discharge machining. Preferably, the stent of the present invention is formed by laser cutting the stent pattern from a flat sheet and then rolling the stent into a cylinder with a longitudinal weld, or by cutting the stent pattern from a solid tubular member, both processes being well known.

Other modifications and improvements may be made without departing from the scope of the invention. For example, the various drawing figures depict several configurations of the stent of the invention including various sizes, which can be modified to suit a particular application without departing from the spirit and scope of the invention. Further, the configuration of the catheter assembly, including a rapid-exchange catheter, can be modified to suit a particular application without departing from the preferred invention. For example, the stent of the invention can be mounted on over-the-wire catheters which are known in the art.

What is claimed:

1. An intravascular stent for use in repairing a body lumen, comprising:

a plurality of cylindrical rings, each ring having a proximal edge and a distal edge so as to define a width, at least some of the rings having curved sections positioned on one of said edges and attached to substantially straight arms extending between said edges, wherein said arms and curved sections define a non-linear pattern extending about a circumference of a ring and wherein the arms have an expandable slit formed therein and wherein said expandable slit is completely surrounded by said at least one arm; and a plurality of links connecting the cylindrical rings.

2. The intravascular stent of claim 1, wherein the stent has a distal end and a proximal end.

3. The intravascular stent of claim 1, wherein the stent has a first delivery diameter and a second expanded diameter for implanting in the body lumen.

4. The intravascular stent of claim 3, wherein the slit in the arms form an opening when the stent is expanded radially outwardly to the second expanded diameter.

5. The intravascular stent of claim 3, wherein the stent does not substantially shorten when expanded.

6. The intravascular stent of claim 1, wherein the links attach only adjacent rings to each other.

7. The intravascular stent of claim 1, wherein the stent is formed from a metal alloy taken from the group of metal alloys consisting of stainless steel, nickel titanium, and nickel-titanium-vanadium.

8. The intravascular stent of claim 1, wherein the arms are formed of a curved section.

9. The stent of claim 1, wherein the stent is self-expanding.

10. The stent of claim 1, wherein the stent plastically deforms when expanded.

* * * * *

UNITED STATES PATENT AND TRADEMARK OFFICE
CERTIFICATE OF CORRECTION

PATENT NO. : 6,440,162 B1
DATED : August 27, 2002
INVENTOR(S) : Daniel L. Cox et al.

It is certified that error appears in the above-identified patent and that said Letters Patent is hereby corrected as shown below:

Column 8,
Line 39, after "ring", add -- , --.
Line 40, delete "and".
Line 40, after "wherein", add -- at least one of the --.
Line 40, change "have", to read -- has --.

Signed and Sealed this

Eighteenth Day of March, 2003

JAMES E. ROGAN
*Director of the United States Patent and Trademark Office*